United States Patent [19]
Kalnberz et al.

[11] 3,977,397
[45] Aug. 31, 1976

[54] SURGICAL COMPRESSION-DISTRACTION INSTRUMENT

[76] Inventors: Viktor Konstantinovich Kalnberz, ulitsa Stendera, 13, kv. 2; Alexandr Nikolaevich Sinitsyn, ulitsa K. Marxa, 70, kv. 1, both of Riga, U.S.S.R.

[22] Filed: Nov. 27, 1974

[21] Appl. No.: 527,865

[52] U.S. Cl. ............................................. 128/92 A
[51] Int. Cl.² .......................................... A61F 5/04
[58] Field of Search ................ 128/92 R, 92 A, 83, 128/84 R, 84 B, 84 C

[56] References Cited
UNITED STATES PATENTS

| | | | |
|---|---|---|---|
| 2,055,024 | 9/1936 | Bittner, Jr. | 128/92 A |
| 2,238,869 | 4/1941 | Haynes | 128/92 A |
| 2,406,987 | 9/1946 | Anderson | 128/92 A |
| 3,727,610 | 4/1973 | Riniker | 128/92 A |

FOREIGN PATENTS OR APPLICATIONS

| | | | |
|---|---|---|---|
| 240,918 | 8/1969 | U.S.S.R. | 128/92 R |

*Primary Examiner*—John D. Yasko
*Attorney, Agent, or Firm*—Haseltine, Lake & Waters

[57] ABSTRACT

An instrument for treating injuries and diseases of bones and joints which incorporates rings with needles passed through bone fragments. Adjacent rings are interconnected by longitudinal permanently sprung members, viz. helical springs and/or rods connected with the rings by means of nuts. To stabilize the structure, strengthening rings composed of separate arches and carrying locking means for additional needles may be inserted into the instrument.

10 Claims, 11 Drawing Figures

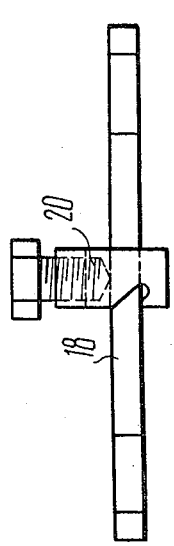
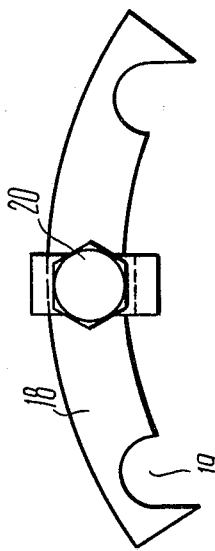
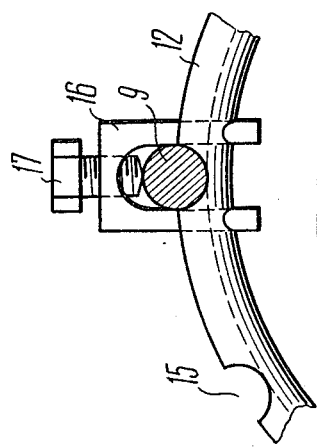
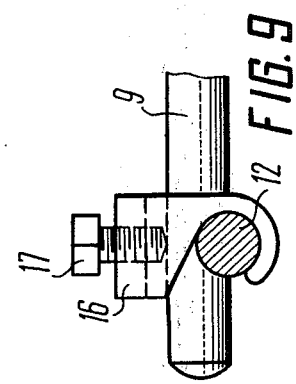

SURGICAL COMPRESSION-DISTRACTION INSTRUMENT

FIELD OF THE INVENTION

The present invention relates to medical equipment and, more particularly, to an improvement in surgical compression-distraction instruments employed for treating injuries and diseases of the locomotorium.

BACKGROUND

All improvement in the various known instruments of this kind have always been aimed, above all, at achieving the maximum possible stability of the broken-off bone fragments fixed in the instrument.

Thus, the original single needle passed through the bone fragment gave way to twin needles. Then the needles were installed in angular relationship or cruciformly. The principle of needle fixation in an arch was discarded in favor of using twin arches or rings. Hempel pioneered the idea of fixing needles in a ring (1929). In the Soviet Union, A. S. Pertsovskii was the first to apply this principle (1938). Ring fixation of needles cruciformly passed through the bone was successfully performed in 1951 by G. A. Ilizarov (U.S.S.R. Inventor's Certificate No. 98,471 with priority, granted June 9, 1952). Elsewhere, Wittmoser in 1953 published his proposal to pass needles fixed in a ring in cruciform manner.

In this way, step by step, from the first days of recognition of the principles of compression and distraction, there has been evolved an independent, extremely promising method of compression-distraction osteosynthesis.

The most advanced and well-tried instruments of Soviet made embodying the above principle are those designed by G. A. Ilizarov, K. M. Sivash and O. N. Gudushauri. The underlying idea behind all practically used compression-distraction designs is a desire to achieve the maximum possible stability of the bone fragments. Of the known instruments, G. A. Ilizarov's one, using simple rings and a cruciform principle of needle introduction, comes closest to the ideal as far as bone fragment stability is concerned.

Most of the known compression-distraction instruments are built around three basic elements.

First of all, there are transaxially passed needles or rods introduced singly, in parallel or in cruciform relationship.

Secondly, there are arches or rings of various forms adapted to fix the ends of the needles or rods.

Thirdly, there are helical rods serving to interconnect the arches or rings of the instrument into a single whole and providing for a proportioned displacement and inclination of the individual arches or rings.

There exist a few designs, however, which use transaxially introduced rods but without recourse to arches or rings for interconnecting same.

At first sight, one may get an impression that the instruments built around the most advanced versions of the three elements described (namely, cruciformly introduced needles, rings and solid helical rods) are the final and optimal solution to all the problems associated with compression-distraction osteosynthesis. G. A. Ilizarov's and Wittmoser's instruments are examples of such designs. However so far the designers have concentrated only on the former two elements — the method of transaxial introduction of needles and the means for fixing the free ends of the needles, such as arches and rings — in their quest for improving compression-distraction instruments, almost entirely overlooking the importance of the helical rods interconnecting the arches and the rings.

Thus, said known instrument designed by G. A. Ilizarov has a serious disadvantage of requiring a complex procedure for matching dislocated bone fragments. Another drawback of this prior art instrument consists in that it is difficult to change the relative positions of the bone fragments in the course of permanent compression (distraction).

Besides, this prior art instrument does not allow additional, e.g. reinforcing, rings to be installed without adversely affecting the compressive (distractive) effect of the instrument.

Still another disadvantage of the known instrument consists in that permanent compression (distraction) of bone fragments cannot be maintained should the needle tension slacken, in cases of ossifluence, needle deformation, etc.

Furthermore, the known instrument does not permit controlling the direction of the instrument axis, bending or straightening it while permanently maintaining compression (distraction).

SUMMARY OF THE INVENTION

It is an object of the present invention to provide a surgical compression-distraction instrument providing for permanence of compression (distraction) of the broken-off bone fragments throughout all adjustments as well as in the course of bone fragment knitting in spite of such adverse factors as slackening of needle tension, ossifluence and deformation of the instrument elements.

A further object of the present invention is to provide a compression-distraction instrument allowing changes in the orientation of one bone fragment with respect to the other in the course of treatment, requiring no dismantling of the instrument.

Still another object of the present invention is to provide a surgical compression-distraction instrument allowing rings and rods to be installed at any desired position of the instrument axis, including a curvilinear position.

Yet another object of the present invention is to provide an instrument amenable to axis shape changes, viz. bending or straightening, with the compression (distraction) effect mantained unchanged.

Another object of the present invention is to provide a surgical compression-distraction instrument combining the advantage of shape adjustability with a fairly simple and cheap design.

These and other objects are attained by the provision of a surgical compression-distraction instrument for treating injuries and diseases of bones and joints, comprising needles passed through bone fragments, rings whereby said needles are fixed, and longitudinal members interconnecting the separate rings, which, in accordance with the present invention, is characterized in that said longitudinal members include springs maintaining the system of rings of the instrument in a state of permanent compressive stress ensuring permanent compression (distraction) of the bone fragments to be knitted.

Such a relatively simple modification of the design of the surgical instrument in question succeeds in considerably improving the effectiveness and versatility of the frame structure.

In accordance with one embodiment of the present invention, the surgical compression-distraction instrument is characterized in that said longitudinal connecting members are formed as helical springs connected by adjusting nuts at every point of intersection with the rings.

The foregoing design solution proves the simplest and most effective if the bone fragments of a joint to be knitted are to be maintained in a state of permanent compression (distraction).

In accordance with another embodiment of the present invention, the surgical compression-distraction instrument is characterized in that said springs are made up of segments with left-hand and right-hand coils, the segments having differently oriented coils being interconnected by nuts which, by being turned, provide for the simultaneous approximation and separation of these segments and the sections of adjoining rings.

This design feature makes for maximum convenience of adjustment of the instrument frame and permits the elements of the structure to be simultaneously and symmetrically displaced.

In accordance with still another embodiment of the present invention, the surgical compression-distraction instrument is characterized in that connecting rods adding to the stiffness of the elastic system of the instrument are passed in parallel with said springs. The latter modification serves to facilitate the task of selecting the required stiffness of the instrument frame.

In accordance with yet another embodiment of the present invention, the surgical compression-distraction instrument is characterized in that said rods are passed within said helical springs and carry nuts on the ends thereof for varying the tension of the spring on each individual rod.

This latter feature permits selectively adjusting the tautness (degree of compression) each individual spring, achieving the required degree of compression (distraction) at a desired shape of the instrument frame.

In accordance with a further embodiment of the present invention, the surgical compression-distraction instrument is characterized in that, in order to stabilize and strengthen the desired structure of the instrument frame, at least some of the rings mounted over the strengthening sections are made up of separate arch members having open seats on the exterior surfaces thereof, said seats serving to receive the longitudinal springs and rods of the instrument, and there are provided clamps for fixing said spring and/or rod in said respective seat as well as for interconnecting the arch members into a full strengthening ring.

Owing to the latter modification, any additional rings may be installed at any required point in the instrument to stabilize and strengthen the instrument frame without requiring the instrument to be dismantled, i.e. with the instrument being ready for operation.

In accordance with a still further embodiment of the present invention, the surgical compression-distraction instrument is characterized in that said sectional rings are constructed from rods of a round cross-section, while said seats are formed as depressions in the outer surfaces of said rods, and the sectional rings carry brackets with fastening screws for fixing the spring or rod in the respective ring seat and for fastening an additional needle to this ring.

The latter feature permits installing additional rings and additional needles in an assembled instrument without affecting the state of compressive stress of the instrument structure.

In accordance with yet another embodiment of the present invention, the surgical compression-distraction instrument is characterized in that, in order to enable an additional needle to be mounted on any desired portion of the ring and at any desired angle, said brackets are mounted on the rings in such a way that they can be previously turned about their respective round rods.

This feature permits an additional needle to be previously turned through any desired angle together with the respective clamp about the respective round rod of the ring, and the clamp to be secured in any required position.

And finally, in accordance with another embodiment of the present invention, the surgical compression-distraction instrument is characterized in that transversal cross bars carrying clamps for additional needles are mounted on adjacent longitudinal members — springs or rods.

This latter feature adds still more to the versatility of the proposed design, as it enables a strengthening needle to be installed in any location in a very simple way.

BRIEF DESCRIPTION OF THE DRAWING

The present invention will be further understood and its advantages more fully appreciated from the following description of several exemplary embodiments of the proposed instrument taken in conjunction with the accompanying drawings, wherein:

FIG. 8 shows a means for locking the instrument rod on an additional ring according to FIG. 5;

FIG. 9 shows a means for locking the instrument rod on an additional ring according to FIG. 5;

FIG. 10 is a plan view of a bracket with a needle lock; and

FIG. 11 is a side elevation of the bracket of FIG. 10.

DETAILED DESCRIPTION

Figure 1:
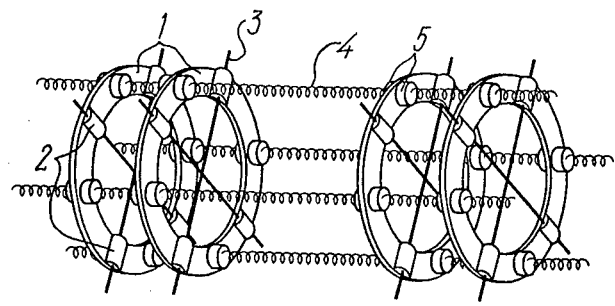
FIG. 1 is a schematic general view of a surgical compression-distraction instrument, in accordance with the invention, with longitudinal spring members.
Figure 2:
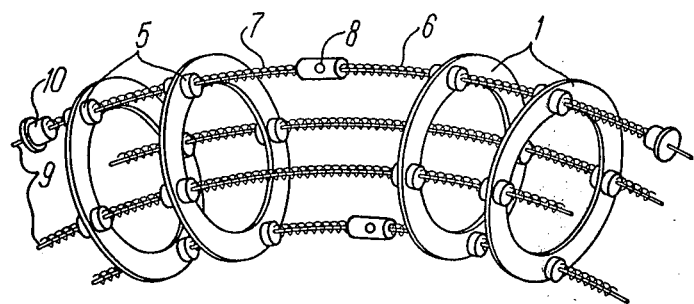
FIG. 2 is an embodiment of the proposed surgical instrument with spring segments having differently oriented coils (the instrument is shown without needles and clamps in a selected curved position)
Figure 3:
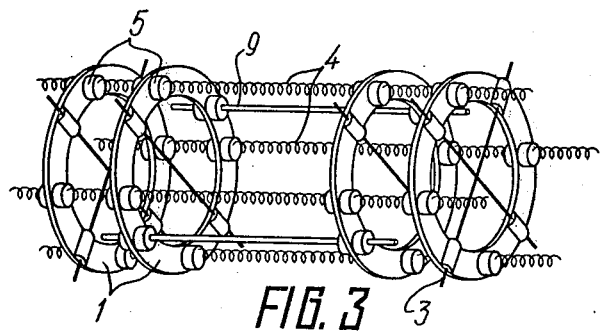
FIG. 3 is an embodiment of the proposed compression-distraction instrument with combined rod-spring members.
Figure 4:
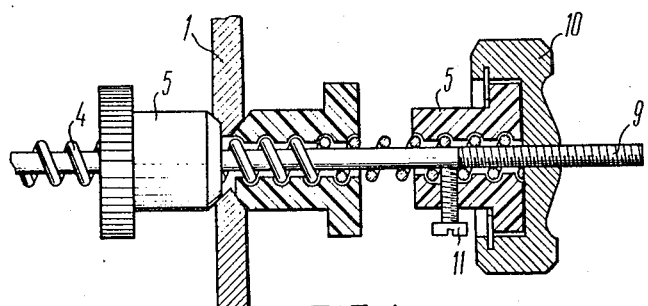
FIG. 4 is a partly cross-sectional view showing the way an instrument with a ring is connected with a spring carrying a rod therewithin (the instrument of FIG. 3)

Referring now to the drawings, it will be seen that the proposed surgical compression-distraction instrument comprises rings 1 (FIG. 1) with clamps 2 for needles 3 mounted on longitudinal load-bearing members formed as helical springs 4 and fixed on the rings 1 by means of nuts 5 whose thread corresponds to the profile of the springs 4. The spring 4 may comprise a spring segment 6 (FIG. 2) with right-hand coils and a spring segment 7 with left-hand coils, the segments 6 and 7 being interconnected by a nut 8 having a left-hand thread and a right-hand thread at the ends thereof. Inside the springs 4 or the spring segments 6 and 7, there may be installed strengthening rods 9. The ends of the rods 9 may be provided with a thread for holding nuts 10 (FIG. 4), the bores of the nuts 10 receiving the smaller nuts 5 fixed by set screws 11. In some cases, ordinary rigid rods 9 (FIG. 3) may be mounted on the ring 1 together with the longitudinal members in the form of helical springs 4 or spring segments 6 and 7.

The instrument of this invention operates as follows:

Having administered an anaesthetic, the bone fragments are matched as accurately as possible. Two or more crossing needles 3 (FIGS. 1–3) are passed through the distal and proximal metaphyses of the bone in a plane perpendicular thereto. The ends of the needles 3 are fastened in a tensioned state by the clamps 2 to the rings 1. The rings 1 are interconnected by members formed as the springs 4, with the nuts 5 brought to the plane of the rings 1. Prior to tightening the nuts 5, the instrument is placed in a required position. In order to bend the instrument this or that way, the inner portions of the rings 1 are approximated by tightening the nuts 5 over the inner section and simultaneously the outer rings 1 are driven apart by loosening the nuts 5 over the outer section of the bend.

Having been installed in a required spatial position, the instrument is operated in a conventional manner. After the instrument has been applied, by displacing the nuts 5 over the respective sections compression is effected stretching the springs 4 or the spring segments 6 and 7 relative to the rings 1 fixed in the bone fragments by means of the needles 3. In order to raise the stiffness of the springs 4, strengthening rods 9 may be previously installed therewithin. The rods 9 may be installed either in all springs 4 or only in some of them. If in the course of treatment the need for the rods 9 is obviated, they can be withdrawn from the springs 4.

In order to change the initial elasticity of the springs 4 (FIG. 4) or to achieve total compression (distraction) along the entire length of the instrument, the ends of the spring 4 are fixed with the nuts 10, with the end of the spring 4 being grasped, and, by releasing the set screw 11, the nut 10 is displaced relative to the rod 9, compressing or stretching the spring 4.

To provide for the compression (distraction) of one of the sections of the instrument by displacing a group of rings 1, the longitudinal members are formed as half-springs, or segments 6 and 7; turning the nut 8 having a right-hand thread and a left-hand thread at the ends thereof, the respective portions of the springs between two adjoining rings 1 are either lengthened or shortened.

In those cases where at some point in the course of treatment the bone fragments are to be additionally stabilized in addition to the longitudinal members formed as helical springs 4 or half-springs, or segments, 6 and 7, ordinary rigid rods 9 such as are employed in the prior art instruments may be installed and subsequently removed.

Thus, the proposed compression-distraction instrument is highly functional. Its design permits placing the bone fragments in any desired positions without relieving compression or distraction. Additionally, the positions of the bone fragments may be altered by changing the state of the instrument rings.

While in the prior art instrument the rod block may be expanded only through lowering the stress and installing additional rods, in the proposed instrument the same objective can be reached either by varying the tension of the screws fixed on the rod ends, or else by moving apart (or together) the crossed springs with the help of specially provided nuts. The instrument of this invention is distinguished by virtue of design simplicity and can be employed to treat both fresh injuries and various orthopaedic diseases.

Figure 5:
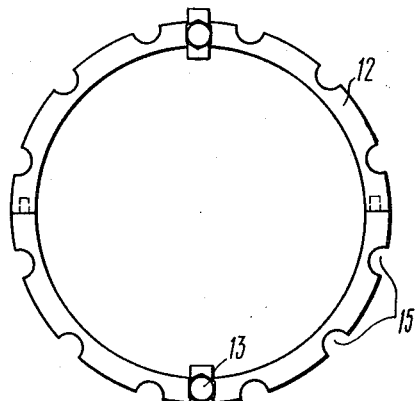
FIG. 5 illustrates a ring of the proposed compression-distraction instrument, in accordance with the invention, shown assembled.
Figure 6:
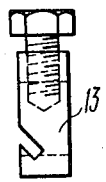
FIG. 6 illustrates a means for locking the needles in the instrument with a ring shown in FIG. 5.
Figure 7:
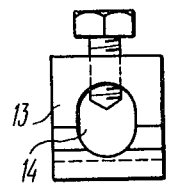
FIG. 7 illustrates a means for locking the needles in the instrument with a ring shown in FIG. 5.

In accordance with the present invention, the compression-distraction instrument may be equipped with an additional lengthwise-split ring 12 (FIG. 5) constructed from rods having a round cross-section. The ring 12 is provided with clamps 13 (FIGS. 5–7) for needles, these clamps are mounted on the ring 12 through round holes 14. On the outer surface of the ring 12 (FIG. 5) there are formed seats 15 receiving the springs 4 (FIGS. 1–3) or the rods 9 of the compression-distraction instrument. The ring 12 is fastened to the rods 9 (FIGS. 8, 9) by means of special locking means 16 formed as brackets and enveloping the ring 12 and the rod 9. The locking means 16 is secured by means of a screw 17. Cross bars 18 (FIGS. 10, 11) having seats 19 for the rods 9 or the springs 4 on the inner surfaces thereof may be installed as additional locking means. The cross bars are likewise provided with clamps 20 for needles, the shape of the holes in the clamps 20 corresponding to the cross-section of the cross bars 18.

The proposed compression-distraction instrument is installed in the following manner:

After the patient's skin has been prepared and an anaesthetic administered, the broken-off bone fragments are matched as accurately as possible. Then two or more needles 3 (FIGS. 1–3) are passed through the distal and proximal metaphyses of the bone and fixed in the rings 1 of the compression-distraction instrument. The rings are interconnected by members formed either as the screws 9 or the springs 4 by means of the nuts 5. Compression is achieved by turning the nuts 5, thereby setting the rings 1 in a desired position, which is done by shortening or lengthening the sections between the springs 4. If additional fixation is required or the stiffness of the springs 4 is to be enhanced, the additional ring 12 (FIG. 5) is mounted in the instrument. Should the ring 12 be needed to change the positions of the bone fragments two or more needles are introduced on the chosen level and fixed to the ring 12 by means of the needle clamps 13. The ring 12 is so positioned in the instrument so that the springs (rods) are received in the seats 15. The ring 12 is fastened to the rods by means of special locking means 16 enveloping the ring 12 and the rod and fixed by tightnening the screw 17. The cross bars 18 may be additionally installed to allow passage of individual needles, the cross bars 18 being so positioned in the instrument above the springs (rods) that the springs (rods) are received in the seats 19, and the needles are secured in the cross bars 18 by means of the needle clamps 20.

Thus, the spring employed in the proposed instrument for the purpose of connecting the rings or the half-rings, in accordance with the invention, can receive in its opening a rod, or core, of various elasticitiy. Springs have already been employed both in skeleton stretching systems and to provide for a constant level of effort in compression-distraction instruments.

However, in the proposed instrument design, the spring is a basic ring-connecting member rather than a supplementary component.

The spring coils constitute a thread for the light plastic nuts securing the rings. When compression is created at the end portions of bone fragments, the spaces between the coils of the spring expand somewhat, and the stretched spring tends to contract, providing for a constant level of the compressive effort.

If the instrument is applied for the purpose of distraction, the spring sections disposed between the rings are compressed, and the thread springs provide for a constant level of the dittractive effort due to the pushing-apart effect.

The 50 coils of the thread spring are about 10 cm long, and the compressive or stretching spring travel over the section described amounts to 1.5 to 2 cm. Over longer sections, such a "respiratory effect" of the spring becomes more marked. Thus, in all the prior art designs the thread itself is a passive component, whereas in the proposed instrument, owing to the use of thread springs, the thread turns into a dynamic element taking an active part in both compression and distraction.

Thread springs have another valuable property, viz. an ability to bend, which facilitates the task of instrument application in cases of pronounced limb deformations. Thanks to the thread springs, the instrument becomes flexible and elastic, the degree of elasticity being adjusted by use of different rods, or cores.

What with its elasticity, the instrument of this invention may be effectively employed in cases of joint contracture with aberration.

At first sight, one may gather the impression that with the use of springs to connect the instrument rings, the fixation loses rigidity with the resultant loss of fixation stability. Actually, however, the proposed instrument ensures elastic-stressed fixation, providing for a higher degree of stability than can be achieved in prior art instruments.

The highest level of fixation "rigidity" is achieved in G. A. Ilizarov's instrument which uses crossed needles and rod-connected rings. The metal components of the instruments can be sufficiently rigidly interconnected (needle ends to rings and rings by means of rods). As for the needles, even cruciformly passed through the bone, the level of rigidity is likely to drop somewhat owing to the resorption of the bony tissue into the needles as well as because of the displacement of individual bone fragments. Besides, the needles themselves are likely to bend, so that in actual use the needle "cross" bends this or that way relative to the ring depending on whether the rings are used in a compressive or distractive mode.

So, the "rigidity" of connection of the separate parts of the compression-distraction instrument is not enough to provide for the "rigidity" of fixation of the bone fragments. This is the reason why it took several rings applied on one limb segment to achieve the required degree of fixation stability.

Where thread springs are used, an elastic-stressed system is provided which ensures a constant level of the compressive or distractive effect. If, for some reason, the needles fixing the bone fragments lose some of their ridigity in between the nut-tightening periods, the thread spring comes into action and restores the lost rigidity.

What is claimed is:

1. A surgical compression-distraction instrument for treating injuries and diseases of bones and joints, comprising: needles adapted for being passed through the bone fragments being joined; rings including attachments for fastening said needles and for rendering the same taut; longitudinal members interconnecting said individual rings to form a single frame with the bone fragments disposed in required positions relative to each other; said longitudinal members being constituted as cylindrical coil springs acting on said rings to maintain same in an elastic state and provide for a constant level of elastic compression of the bone fragments whose union is to be achieved, and adjusting nuts connecting said coil springs to said rings to permit angular and axial adjustment of said rings relative to one another by virtue of the elasticity of the coil springs connecting said rings.

2. A surgical compression-distraction instrument as claimed in claim 1, comprising nuts and wherein said springs include segments with left-hand and right-hand coils, the segments with differently oriented coils being interconnected by means of at least some of said nuts which, when turned, provide for the approximation or separation of these segments and the sections of adjoining rings.

3. A surgical compression-distraction instrument as claimed in claim 1, comprising elastic connecting rods connecting at least some of said rings for adding to the rigidity of the elastic system of the instruments, said rods being in parallel with said springs.

4. A surgical compression-distraction instrument as claimed in claim 1, wherein, to stabilize and strengthen the required structure of the instrument frame, at least some of the rings installed over the strengthening sections being in the form of half-rings having open seats on the outer surfaces thereof, said open seats being adapted to receive the longitudinal springs and the rods of the instrument, said instrument further comprising clamps for fixing the longitudinal member in the respective seat as well as for interconnecting said half-rings into a full strengthening ring.

5. A surgical compression-distraction instrument as claimed in claim 4, comprising brackets including set screws and wherein said sectional rings are of a round cross-sections, said seats being depressions in the outer surfaces of said round rings, the sectional rings carrying said brackets with said set screws for securing the longitudinal springs or additional needles to this ring.

6. A surgical compression-distraction instrument as claimed in claim 5, wherein, in order to enable said additional needle to be fixed on any portion of the ring and at any desired angle, said respective brackets are so dimensioned and arranged as to be adapted to be previously turned about the respective round ring.

7. A surgical compression-distraction instrument as claimed in claim 1, comprising transversal cross bars and clamps thereon for additional needles, said cross bars being mounted on the adjacent longitudinal members.

8. A surgical compression-distraction instrument, as claimed in claim 1, comprising elastic rods mounted within said cylindrical springs, and adjusting nuts on the ends of said rods to vary the spring tension on each individual rod.

9. A surgical compression-distraction instrument as claimed in claim 4, wherein said half rings are circular in cross-section, and the seats are formed as depressions in the outer surface thereof, said clamps including clips with fixing nuts to fix the longitudinal members and additional needles to the ring.

10. A surgical compression-distraction instrument as claimed in claim 8, comprising transverse cross-bars carrying clamps for additional needles mounted on adjacent longitudinal members, springs or rods.

* * * * *